United States Patent [19]

Giersch et al.

[11] 4,396,781
[45] Aug. 2, 1983

[54] UNSATURATED ALICYCLIC ETHERS

[75] Inventors: Wolfgang Giersch; Günther Ohloff, both of Bernex, Switzerland

[73] Assignee: Firmenich SA, Geneva, Switzerland

[21] Appl. No.: 98,748

[22] Filed: Nov. 30, 1979

[30] Foreign Application Priority Data

Dec. 21, 1978 [CH] Switzerland ............... 12989/78

[51] Int. Cl.³ .................................. C07C 43/188
[52] U.S. Cl. ........................... 568/667; 252/522 R; 131/276
[58] Field of Search ............... 568/667; 252/522 R

[56] References Cited

U.S. PATENT DOCUMENTS 3,586,727 6/1971 Wilke et al. ............ 568/667 X
3,801,600 4/1974 Naegeli ................ 252/522 R X
3,876,561 4/1975 Naegeli ................ 252/522 R Primary Examiner—Bernard Helfin
Attorney, Agent, or Firm—Pennie & Edmonds

[57] ABSTRACT

New compounds of formula

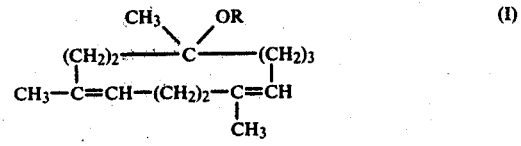

wherein symbol R represents a lower alkyl radical and use thereof as perfuming and flavoring ingredients. Process for the preparation of the said compounds.

3 Claims, No Drawings

UNSATURATED ALICYCLIC ETHERS

BRIEF SUMMARY OF THE INVENTION

The instant invention relates to the fields of perfumery and of the flavor industry, in particular it relates to unsaturated alicyclic ethers of formula

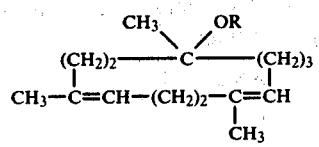

wherein symbol R represents a lower alkyl radical and to the use thereof as perfuming and flavoring ingredients.

BACKGROUND OF THE INVENTION

The palette of perfumers and flavorists is constantly enriched by the discovers of novel active substances whose original characters enable the creation of new compositions or the replacement of more costly materials.

Among the variety of chemicals known in the art of perfumery, macrocyclic compounds are recognized as ingredients of choice. This class of derivatives include cyclopentadecanone (EXALTONE®), muscone or pentadecanolide (EXALTOLIDE®), which compounds are appreciated in the art for their particularly tenacious musky odor. Several derivatives of cyclododecane have also been described. For instance, the compounds of formula

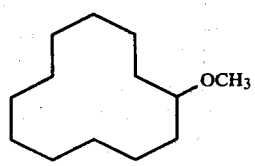

and of formula

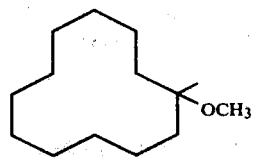

[see Pat. No. 443,536 and DE-OS No. 21 52 016, respectively] are utilized for the reconstitution of odorous notes of woody, cedar or amber type.

DE-AS No. 12 23 974 and UK Pat. No. 937,976 describe the utilization of the methyl esters of formula

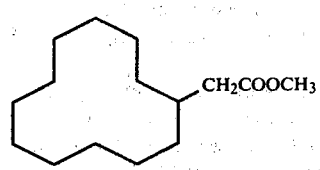

and

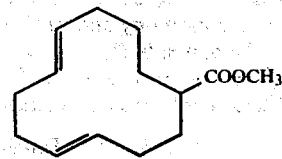

which compounds are characterized by a woody fragrance of rose type and of vetiver type, respectively. Other examples of woody type macrocyclic compounds include the unsaturated alicyclic derivatives of formula

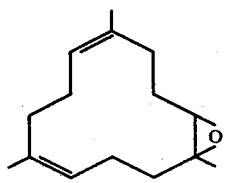

and

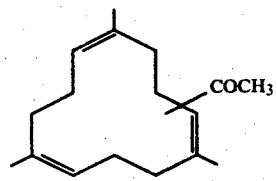

and their corresponding isomers [see Swiss Pat. No. 487,240 and U.S. Pat. No. 3,816,349].

Irrespective of the prior described perfume ingredients there was a constant need for perfumants having a woody character. We have discovered that the new unsaturated alicyclic compounds of formula

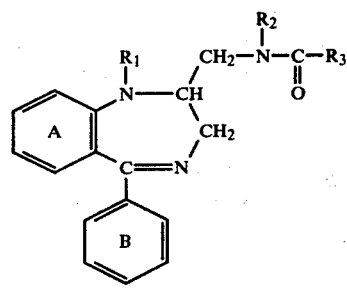

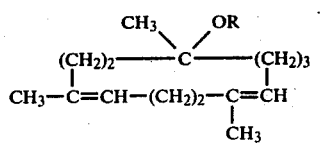

wherein symbol R represents a lower alkyl radical, possessed useful organoleptic properties and consequently they could be advantageously used in the perfume and flavor industry.

When used as perfumants, compounds (I) are characterized by a tenacious woody scent reminiscent of the odor of patchouli.

The characteristic woody, patchouli note of the said compounds rarely becomes dominant and they can be advantageously utilized for the manufacture of chypre, rose, woody or fougère compositions, to which they confer harmony and richness.

Compounds (I) can be used for the preparation of perfumed products such as e.g. soaps, detergents, household materials or cosmetic preparations.

PREFERRED EMBODIMENTS OF THE INVENTION

The proportions in which the compounds of the invention can produce the desired perfuming effects can vary within wide limits. Typically, for the manufacture of perfume compositions, these proportions are of about 1 to 30% by weight, occasionally they can be of 50% or even more for the preparation of perfume bases or perfume "coeurs". It has to be appreciated however that these concentration values are not deemed to be interpreted restrictively and values higher or lower than those indicated can also be used.

In the flavor field, compounds of formula (I) are characterized by a taste and an aroma which could be defined as woody and amber-like. They can advantageously be used in the manufacture of various artificial flavors and more particularly for the aromatization of tobacco or tobacco products to which they confer a woody and amber-like flavor reminiscent of the taste and aroma of oriental tobacco.

The nature, the solubility and the stability of compounds (I) determine the conditions for their utilization. They can be incorporated in the course of any step of the manufacture of the tobacco articles, preferably after the processes of aging, drying and cutting of tobacco leaves and before the manufacture of cigarettes.

The usual technique for tobacco aromatization consists in spraying the chosen mixture of tobaccos with a solution of the flavorants in ethanol or in a mixture of ethanol and propylene-glycol.

To this effect, proportions of the order of 1 to 500 ppm, (parts per million) preferably of 10 to 100 ppm, by weight based on the total weight of the aromatized material can be conveniently used. These proportions are set forth for the purpose of illustration only and are not to be interpreted restrictively.

The instant invention relates also to a process for the preparation of the compounds of formula (I) which consists in reacting, in the presence of an acid catalyst, 2,5,9-trimethyl-cyclododeca-1,5,9-triene with a hydroxylic compound of formula

R—OH  (II)

wherein symbol R designates a lower alkyl-radical.

The reaction is carried out in accordance with the usual techniques normally applied to the preparation of aliphatic ethers starting from olefins. Suitable acid catalysts include strong mineral or organic acids, e.g. sulfuric acid, p-toluene-sulfonic acid, or an acidic diatomaceous earth. The reaction can be effected in the presence of an inert organic solvent, or more frequently however, in the presence of an excess of hydroxylic compounds (II). Moreover, the reaction is carried out at a temperature ranging in the vicinity of the boiling point of the chosen reaction mixture.

Due to the presence of two olefinic double bonds in positions 4 and 8 of their molecule, the compounds of formula (I) resulting from the above described process can occur under different isomeric forms, and formula (I) generally designates any of said isomers. 

2,5,9-Trimethyl-cyclododeca-1,5,9-triene used as starting material in the above described process is a commercially available material which results from the catalytic trimerization of isoprene.

The terms "lower alkyl radical" used throughout this specification is deemed to include methyl, ethyl, n-propyl, isopropyl, n-butyl, sec-butyl, ter-butyl.

The invention is further illustrated by, but not limited to, the following examples wherein the temperatures are indicated in degrees centigrade.

EXAMPLE 1

1-Methoxy-1,4,8-trimethyl-cyclododeca-4,8-diene 340 g (1.67 M) of 2,5,9-trimethyl-cyclododeca-1,5,9-triene and 110 g of acidic diatomaceous earth in 5000 ml of methanol (containing less than 0.05% of water) were refluxed during 40 h. After cooling at room temperature and filtration, the mixture was concentrated at reduced pressure to yield, after a distillation, 366 g of a product having b.p. 79°–110°/0.01 Torr. After fractional distillation, 212 g of starting 2,5,9-trimethylcyclododeca-1,5,9-triene (b.p.43°–52°/0.1 Torr) and 140 g of the desired product, b.p. 78°–82°/0.01 Torr (yield 95% based on the converted starting material).

IR (film): 1470 cm$^{-1}$.

NMR: signals at 1.1, 1.6, 3.2 and 5.2 δ ppm.

MS: M+ =236 (11); m/e=221 (3), 204 (59), 189 (37), 175 (15), 161 (27), 147 (31), 133 (28), 121 (51), 107 (100), 93 (86), 85 (98), 67 (66), 55 (85), 41 (92).

EXAMPLE 2

1-Ethoxy-1,4,8-trimethyl-cyclododeca-4,8-diene 550 g (2.7 M) of 2,5,9-trimethyl-cyclododeca-1,5,9-triene and 380 g of acidic diatomaceous earth in 6250 ml of anhydrous ethanol were refluxed for 72 h to give, after the same treatment as that described in Example 1 above, 532 g of a product having b.p. 70°–110°/0.01 Torr. On fractional distillation, there were recovered 495 g of starting 2,5,9-trimethyl-cyclododeca-1,5,9-triene (b.p. 43°–52°/0.1 Torr) and 42.5 g of the desired product (b.p. 90°–105°/0.01 Torr); yield 63% based on the converted starting material.

IR (film): 1450 cm$^{-1}$.

NMR: signals at 3.4 and 5.2 δ ppm.

MS: M+=250 (9); m/e=235 (6), 204 (44), 189 (21), 161 (29), 139 (98), 121 (34), 107 (59), 95 (68), 81 (72), 67 (50), 55 (67), 43 (100).

EXAMPLE 3

5 ml of 0.1% solution of 1-methoxy-1,4,8-trimethyl-cyclododeca-4,8-diene in 95% ethanol were sprayed onto 100 g of a tobacco mixture of "American blend" type. The tobacco thus flavored was then used for the manufacture of "test" cigarettes, the smoke of which was subjected to an organoleptic evaluation by a panel of flavor experts. The panel declared that the smoke of the "test" cigarettes, when compared with the "control" cigarettes, possessed an enhanced woody and amber-like note reminiscent of the taste and aroma of oriental tobacco.

By replacing, in the example above, 1-methoxy-1,4,8-trimethyl-cyclododeca-4,8-diene with an equivalent amount of 1-ethoxy-1,4,8-trimethyl-cyclododeca-4,8-diene, an analogous effect was observed.

EXAMPLE 4

A base perfume composition for Eau de Cologne was prepared by mixing the following ingredients (parts by weight):

| | |
|---|---|
| Lemon oil | 250 |
| Bergamot oil | 300 |
| Orange oil | 150 |
| Petitgrain Bigarade | 100 |
| Neroli Bigarade | 20 |
| Lavender oil | 70 |
| White thyme oil | 10 |

By diluting the above base, in a proportion of 3% (by weight) in 95% ethanol, "classical" Eau de Cologne was obtained.

A novel composition was obtained by adding 0.25 g of 1-ethoxy-1,4,8-trimethyl-cyclododeca-4,8-diene to 100 g of the above Eau de Cologne. Its odor was more tenacious, rounder and more pleasant.

By replacing 1-ethoxy-1,4,8-trimethyl-cyclododeca-4,8-diene with an equal quantity of the corresponding 1-methoxy-derivative, similar effects were observed.

EXAMPLE 5

A base perfume composition of "wood" type was prepared by mixing the following ingredients (parts by weight):

| | |
|---|---|
| 1-ethoxy-1,4,8-trimethyl-cyclododeca-4,8-diene | 500 |
| Methyl dihydro-abietate | 150 |
| p-ter-Butyl-cyclohexyl acetate | 100 |
| α-Iso-methyl-ionone | 100 |
| Absolute oak moss 10%* | 30 |
| αPinene | 30 |
| 4-Methyl-4-phenyl-pent-2-yle acetate 10%* | 20 |
| Elemol | 20 |
| RHUBOFIX ® (Firmenich SA)[1] | 10 |
| Acetaldehyde-phenylethyl propyl acetal | 10 |
| β-Damascone 10%* | 10 |
| AMBROX ® (Firmenich SA)[2] 1%* | 10 |
| β-Damascenone 1%* | 5 |
| Methyl-nonyl-acetaldehyde | 5 |
| Total | 1000 | in diethyl phthalate
[1] mixture of 9(9,12-epoxyethyl)-4- and -5-methyl-tricyclo [6.2.1.0$^{2,7}$] undec-4-ene [see e.g. Swiss Pat. No. 547,850.]
[2] 3-methyl-dodecahydro-6,6,9-trimethylnaphtho-(2,1) furane [see U.S. Pat. No. 3,029,255.]

The thus prepared base was characterized by a strong and tenacious odour reminiscent of freshly cut wood.

EXAMPLE 6

A base perfume composition of "Fougère" type was prepared by mixing the following ingredients (parts by weight):

| | |
|---|---|
| Lavandin oil | 250 |
| Coumarin | 80 |
| Synthetic geranium oil | 80 |
| Absolute oak moss 50%* | 80 |
| Benzyl benzoate | 60 |
| Synthetic bergamot oil | 50 |
| Rose wood oil of Brazil | 50 |
| Terpenyl acetate | 40 |
| Amyl salicylate | 40 |
| Isobutyl benzoate | 30 |
| Terpineol | 20 |
| Aspic oil | 20 |
| Clove oil | 20 |
| Ambrette musk | 10 |
| EXALTEX ® (Firmenich SA) | 10 |
| Galbanum resinoid | 5 |
| MAYOL ® (Firmenich SA)[1] | 5 |
| Total | 800 |

*in diethyl phthalate
[1] 4-Isopropyl-cyclohexylmethanol [see Swiss Pat. No. 578,312.]

This Fougère type base, typically incorporated e.g. in toilet soaps, in characterized by the absence of woody perfumants such as cedar or patchouli oil. The woody character could be conferred by adding 20 g of 1-ethoxy-1,4,8-trimethyl-cyclododeca-4,8-diene to 80 g of the said base. The thus obtained composition possessed a richer and more harmonious scent and a slightly woody tonality.

By replacing, in the above example, 1-ethoxy-1,4,8-trimethyl-cyclododeca-4,8-diene by an identical amount of 1-methoxy-1,4,8-trimethyl-cyclododeca-4,8-diene, an analogous effect was observed.

EXAMPLE 7

1-Methoxy-1,4,8-trimethyl-cyclododeca-4,8-diene was used to perfume standard articles in the concentration given below. The stability and the color of the resulting perfumed articles on storage are indicated in the following table:

| Article | Concentration by weight | Temperature [°C.] | Performances stab. color |
|---|---|---|---|
| Eau de Cologne | 5% in 95% ethanol | 22 | S/N* |
| Soap | 0.5% | 22 | S |
|  |  | 40 | S |
| Talc | 1% | 22 | S/N |
| Deodorizer | 1.2% | 22 | S/N |
| Non-fatty cream | 0.4% | 22 | S/N |
| Shampoo | 0.5% | 22 | S/N |

*S = stable
N = normal

What we claim is:
1. Unsaturated alicyclic compounds of formula

$$\begin{array}{c} CH_3 \quad OR \\ \diagdown \diagup \\ (CH_2)_2 \text{———} C \text{———} (CH_2)_3 \\ | \qquad\qquad\qquad\qquad | \\ CH_3\text{—}C\text{=}CH\text{—}(CH_2)_2\text{—}C\text{=}CH \\ | \\ CH_3 \end{array} \quad (I)$$

wherein symbol R represents a lower alkyl radical.
2. The compound according to claim 1 wherein symbol R represents a methyl radical.
3. The compound according to claim 1 wherein symbol R represents an ethyl radical.

* * * * *

UNITED STATES PATENT AND TRADEMARK OFFICE
CERTIFICATE OF CORRECTION

PATENT NO. : 4,396,781
DATED : Aug. 2, 1983
INVENTOR(S) : Wolfgang Giersch; Gunther Ohloff It is certified that error appears in the above-identified patent and that said Letters Patent is hereby corrected as shown below:

At column 2, lines 40-50, delete Formula I.

Signed and Sealed this

Twenty-fourth Day of January 1984

[SEAL]

Attest:

GERALD J. MOSSINGHOFF

*Attesting Officer*  *Commissioner of Patents and Trademarks*